United States Patent
Nobutani et al.

(10) Patent No.: US 10,102,420 B2
(45) Date of Patent: Oct. 16, 2018

(54) INFORMATION PROCESSING SYSTEM, INFORMATION PROCESSING METHOD, AND ELECTRONIC DEVICE

(71) Applicant: FUJI XEROX CO., LTD., Tokyo (JP)

(72) Inventors: Naoya Nobutani, Kanagawa (JP);
Manabu Hayashi, Kanagawa (JP);
Masafumi Ono, Kanagawa (JP);
Kunitoshi Yamamoto, Kanagawa (JP);
Toru Suzuki, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/206,998

(22) Filed: Jul. 11, 2016

(65) Prior Publication Data
US 2017/0277939 A1    Sep. 28, 2017

(30) Foreign Application Priority Data
Mar. 28, 2016  (JP) ................. 2016-064601

(51) Int. Cl.
*G06K 9/00* (2006.01)
*H04N 1/00* (2006.01)
*H04N 1/44* (2006.01)

(52) U.S. Cl.
CPC ..... *G06K 9/00288* (2013.01); *H04N 1/00854* (2013.01); *H04N 1/442* (2013.01)

(58) Field of Classification Search
None
See application file for complete search history.

(56) References Cited

U.S. PATENT DOCUMENTS

| | | | | |
|---|---|---|---|---|
| 2010/0232653 A1* | 9/2010 | Muquit | .................. | G06F 21/32 382/116 |
| 2011/0205016 A1* | 8/2011 | Al-Azem | ............ | H04L 63/0861 340/5.52 |
| 2016/0180068 A1* | 6/2016 | Das | ........................ | G06F 21/32 726/7 |

FOREIGN PATENT DOCUMENTS

| | | |
|---|---|---|
| JP | 2004-139561 A | 5/2004 |
| JP | 2014-006750 A | 1/2014 |

* cited by examiner

*Primary Examiner* — Sumati Lefkowitz
*Assistant Examiner* — David Perlman
(74) *Attorney, Agent, or Firm* — Oliff PLC

(57) ABSTRACT

An information processing system includes a verification unit and an execution unit. The verification unit verifies biometric information acquired from users against preregistered reference information. The execution unit executes a process based on the number of times biometric information has been verified on a user basis in a predetermined period by the verification unit.

4 Claims, 3 Drawing Sheets

INFORMATION PROCESSING SYSTEM, INFORMATION PROCESSING METHOD, AND ELECTRONIC DEVICE

CROSS-REFERENCE TO RELATED APPLICATIONS

This application is based on and claims priority under 35 USC 119 from Japanese Patent Application No. 2016-064601 filed Mar. 28, 2016.

BACKGROUND

Technical Field

The present invention relates to an information processing system, an information processing method, and an electronic device.

SUMMARY

According to an aspect of the invention, there is provided an information processing system including a verification unit and an execution unit. The verification unit verifies biometric information acquired from users against preregistered reference information. The execution unit executes a process based on the number of times biometric information has been verified on a user basis in a predetermined period by the verification unit.

BRIEF DESCRIPTION OF THE DRAWINGS

Exemplary embodiments of the present invention will be described in detail based on the following figures, wherein.

DETAILED DESCRIPTION

An example of an exemplary embodiment according to the present invention will be described.

Figure 1:
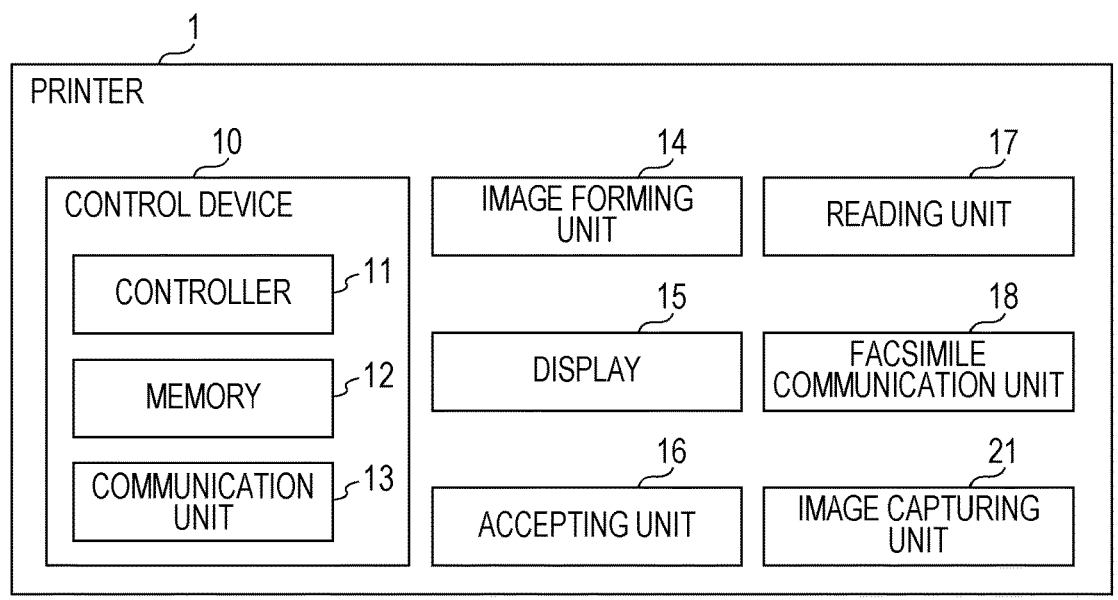
FIG. 1 is a diagram illustrating a hardware configuration of a printer.

FIG. 1 is a diagram illustrating a hardware configuration of a printer 1. The printer 1 is an example of an electronic device according to an exemplary embodiment of the present invention. A control device 10 includes a controller 11, a memory 12, and a communication unit 13, and controls the printer 1. Note that the control device 10 may be configured as an external device of the printer 1, and the control device 10 and the printer 1 may communicate with each other using a communication method.

The controller 11 includes an arithmetic unit such as a central processing unit (CPU), and a storage device such as a read-only memory (ROM) and a random-access memory (RAM). The ROM stores firmware in which a start-up procedure for hardware and an operating system (OS) is described. The RAM stores data used when the CPU executes calculations. The memory 12 includes, for example, a hard disk storage device, and stores an OS, an application program, and the like. The communication unit 13 is a communication interface (I/F) for connecting the printer 1 to a local area network (LAN).

An image forming unit 14 forms, on a sheet-like recording medium, an image based on raster data using, for example, an electrophotographic system or an ink-jet system. The recording medium is, for example, a piece of paper for printing (hereinafter referred to as a paper sheet).

A display 15 includes, for example, a liquid crystal display device, and displays a graphical user interface (GUI) screen for operating the printer 1. An accepting unit 16 includes, for example, a touch panel provided so as to cover a display surface of the display 15, and accepts an operation performed for the printer 1.

A reading unit 17 includes, for example, an image scanner, and optically reads a document and outputs an image signal. The reading unit 17 may also include a document feeding device that feeds stacked documents on a one-sheet basis to a reading position.

A facsimile communication unit 18 includes, for example, a modem connected to a telephone line, and transmits and receives image data to and from a facsimile.

An image capturing unit 21 is for example a digital still camera, and is provided at a position from which at least a face portion of a user operating the printer 1 is included in an angle of view.

Figure 2:
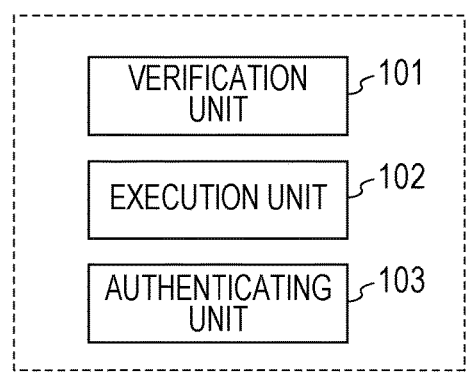
FIG. 2 is a diagram illustrating a functional configuration of the printer.

FIG. 2 is a diagram illustrating a functional configuration of the printer 1. The printer 1 includes a verification unit 101 that verifies biometric information acquired from a user against preregistered reference information, and an execution unit 102 that executes a process based on the number of times biometric information has been verified on a user basis in a predetermined period by the verification unit 101.

In the case where the first verification of a user in the above-described period has been performed by the verification unit 101 and has been successful, the execution unit 102 records information regarding the user. In the case where the verification unit 101 has performed the second or a subsequent verification of the user in the above-described period, the execution unit 102 executes a predetermined process.

<First Exemplary Embodiment>

Figure 3:
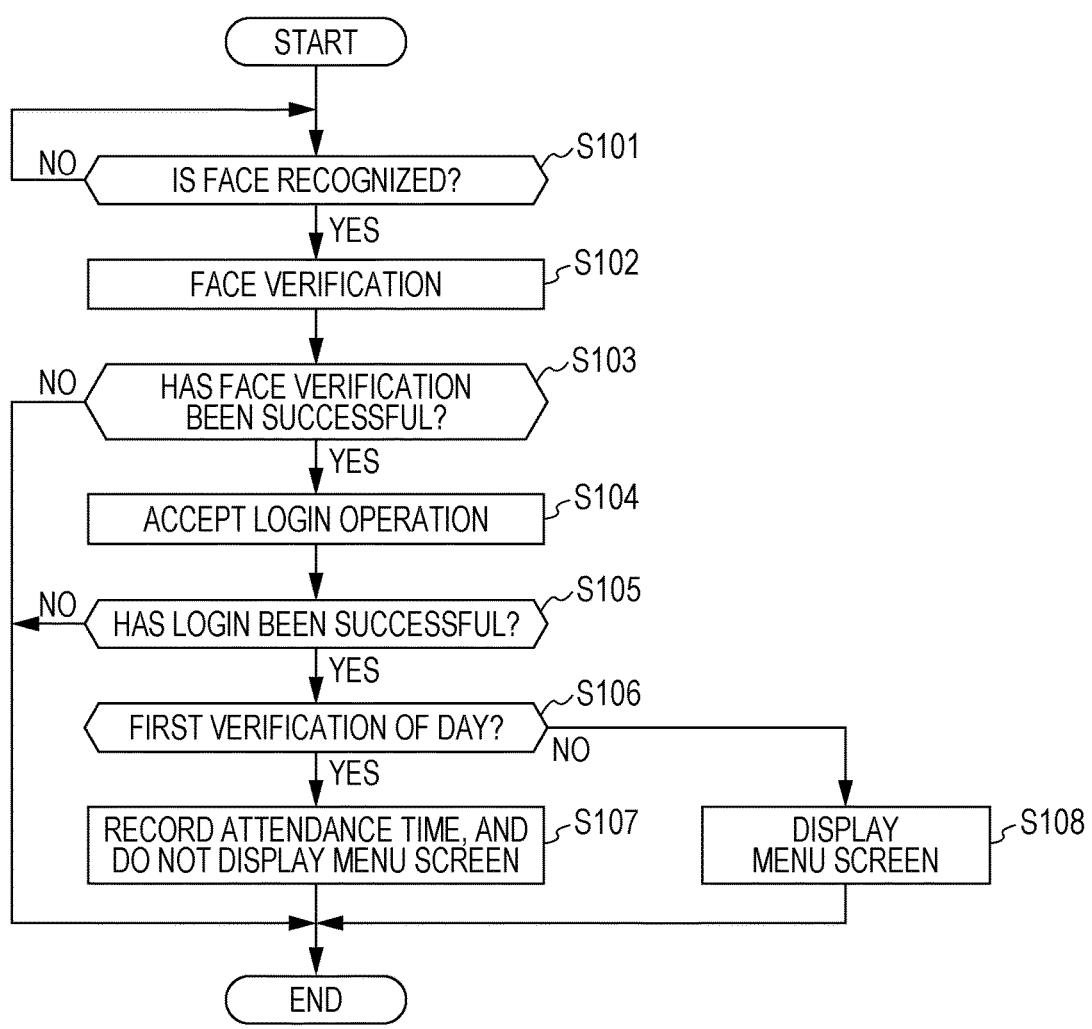
FIG. 3 is a flowchart illustrating an operation according to a first exemplary embodiment.

FIG. 3 is a flowchart illustrating an operation according to a first exemplary embodiment. The controller 11 of the printer 1 executes the following process in accordance with an application program installed in the printer 1.

<Step S101>

The controller 11 determines whether a face is recognized. Specifically, an image captured by the image capturing unit 21 is analyzed, and in the case where the image includes characteristics (the outline, skin color, and so on) common to human faces, it is determined that a face is recognized (YES in step S101) and the process performed by the controller 11 proceeds to step S102.

<Step S102>

The controller 11 executes a face verification (an example of the verification unit 101). Specifically, the memory 12 stores pieces of reference information representing feature values (biometric information) of images of the faces of users who are employees of a business establishment in which the printer 1 is installed. In addition, for each piece of reference information, a counter indicating the number of times a verification has been performed in a day is associated with the piece of reference information. The controller 11 calculates a feature value of the image of the face recognized in step S101, and verifies this feature value against the reference information.

<Step S103>

The controller 11 determines whether the face verification has been successful. Specifically, the controller 11 determines, in the case where the feature value of the image of the face recognized in step S101 corresponds to any of the pieces of reference information, that the face verification has been successful (YES in step S103). The counter corresponding to the corresponding piece of reference information is incremented by one, and the process performed by the controller 11 proceeds to step S104. In the case where the face has not been verified (NO in step S103), the process performed by the controller 11 ends.

<Step S104>

The controller 11 accepts a login operation. Specifically, the controller 11 displays on the display 15 a login screen for entering a user ID and a password. The user enters a user ID and a password into the accepting unit 16.

<Step S105>

The controller 11 determines whether the login has been successful (an example of an authenticating unit 103). Specifically, pairs of user IDs and passwords of users are stored in the memory 12. In the case where the pair of the user ID and the password accepted by the accepting unit 16 corresponds to any of the pairs stored in the memory 12, the controller 11 determines that the login has been successful (YES in step S105), and the process performed by the controller 11 proceeds to step S106. In the case where the login has been failed (NO in step S105), the process performed by the controller 11 ends.

<Step S106>

The controller 11 determines whether this verification of the face of the user is the first verification of the day for the user in accordance with the value of the counter associated with the reference information. In the case where this verification of the face of the user is the first verification of the day for the user (YES in step S106), the process performed by the controller 11 proceeds to step S107. In the case where this verification of the face of the user is the second or a subsequent verification of the day for the user (NO in step S106), the process performed by the controller 11 proceeds to step S108.

<Step S107>

The controller 11 stores an attendance time of the user in association with the user ID (an example of the execution unit 102). Here, the controller 11 does not allow the display 15 to display a menu screen for operating the image forming unit 14, the reading unit 17, the facsimile communication unit 18, and so on.

<Step S108>

The controller 11 causes the display 15 to display the menu screen for operating the image forming unit 14, the reading unit 17, the facsimile communication unit 18, and so on (an example of the execution unit 102).

The operation above is the operation according to the first exemplary embodiment.

<Second Exemplary Embodiment>

Figure 4:
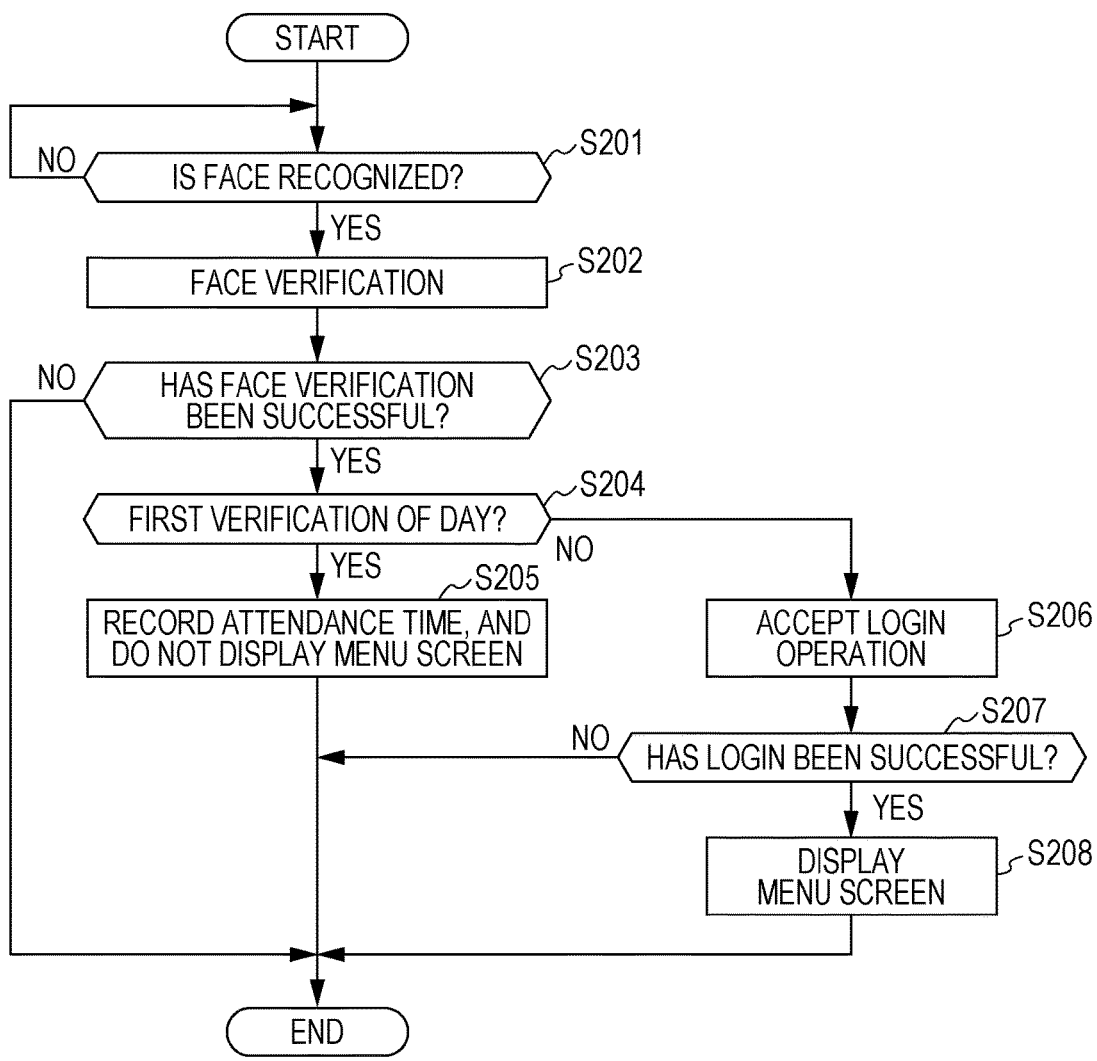
FIG. 4 is a flowchart illustrating an operation according to a second exemplary embodiment.

FIG. 4 is a flowchart illustrating an operation according to a second exemplary embodiment. The operation from step S201 to step S203 is the same as the operation from step S101 to step S103 of the first exemplary embodiment. In the second exemplary embodiment, in the case where the verification unit 101 has performed the second or a subsequent verification of a user and where the authentication performed by the authenticating unit 103 has been successful, the execution unit 102 executes the predetermined process.

<Step S204>

The controller 11 determines whether the verification of the face of the user is the first verification of the day for the user in accordance with the value of the counter associated with the reference information. In the case where this verification of the face of the user is the first verification of the day for the user (YES in step S204), the process performed by the controller 11 proceeds to step S205. In the case where this verification of the face of the user is the second or a subsequent verification of the day for the user (NO in step S204), the process performed by the controller 11 proceeds to step S206.

<Step S205>

The controller 11 stores an attendance time of the user in association with a user ID (an example of the execution unit 102). Here, the controller 11 does not allow the display 15 to display a menu screen for operating the image forming unit 14, the reading unit 17, the facsimile communication unit 18, and so on.

<Step S206>

The controller 11 accepts a login operation. Specifically, the controller 11 displays on the display 15 a login screen for entering a user ID and a password. The user enters a user ID and a password into the accepting unit 16.

<Step S207>

The controller 11 determines whether the login has been successful (an example of the authenticating unit 103). Specifically, pairs of user IDs and passwords of users are stored in the memory 12. In the case where the pair of the user ID and the password accepted by the accepting unit 16 corresponds to any of the pairs stored in the memory 12, the controller 11 determines that the login has been successful (YES in step S207), the process performed by the controller 11 proceeds to step S208. In the case where the login has been failed (NO in step S207), the process performed by the controller 11 ends.

<Step S208>

The controller 11 causes the display 15 to display the menu screen for operating the image forming unit 14, the reading unit 17, the facsimile communication unit 18, and so on (an example of the execution unit 102).

The operation above is the operation according to the second exemplary embodiment.

The above-described exemplary embodiments may be modified into the following modifications. Multiple modifications may also be combined.

<First Modification>

There may be a case where a user whose first face verification of the day has been performed happens to spend some time near the printer 1 by chance even though the user has no intention of using the printer 1, and as a result the second face verification of the user is performed in a short period of time. In this case, display of the menu screen is unnecessary. Thus, after the first face verification of the day for the user is performed, the processing of step S108 in the first exemplary embodiment (display of the menu screen) or the processing (login) in and after step S206 of the second exemplary embodiment may not be executed in the case where the second face verification of the day for the same user is performed within a short period of time (for example, within five minutes).

<Second Modification>

The examples of face verification are described as examples of verification of biometric information in the exemplary embodiments; however, a verification may be performed using biometric information such as a fingerprint, a vein, an iris, or the like.

<Third Modification>

The examples in which the process based on the number of times biometric information has been verified on a user basis in a day is executed have been described in the exemplary embodiments; however, a process based on the number of times biometric information has been verified on a user basis in a certain period such as a week, a month, a half-day may also be executed.

<Fourth Modification>

A process based on the number of errors that have occurred during a face verification may also be executed. An error occurs in a face verification in the case where reference information corresponding to a feature value (biometric information) of a captured image of a face has not yet been registered. When an error occurs, the controller 11 refers to the memory 12. When error information indicating the feature value is not stored, the memory 12 is caused to store the feature value as error information, a counter indicating the number of errors corresponding to this error information is incremented by one, and the display 15 is caused to display a message leading a user to register the feature value. When the user agrees to the registration, the controller 11 registers the feature value as reference information, and deletes the error information and the counter value. When the user disagrees to the registration, the controller 11 keeps retaining the error information and the counter value.

In the case where this user tries a face verification without registration of the feature value, the error occurs again. The controller 11 executes a process different from the process executed at the time of the first occurrence of the error in the case where the error information corresponding to the feature value for which the error has occurred is stored. For example, any of the following processes is performed: (1) the display 15 is caused to display a solution to the error; (2) a display of an information processing apparatus of an administrator is caused to display a message indicating that the error has occurred for the same user multiple times; (3) the display 15 is caused to display a message leading the user to perform authentication using a user ID and a password; and the like. Alternatively, the content of the process may be varied such that (1) is executed in the case where the error has occurred for the second time, and (2) is executed in the case where the error has occurred for the third time.

<Fifth Modification>

A modification according to the present invention may also be applied at the reception of a medical institution. For example, in the case where reference information corresponding to a feature value (biometric information) of a captured image of the face of a patient has not yet been registered, the controller 11 determines that the patient is a first-time patient, causes the display 15 to display a message leading the patient to perform a procedure for a first-time patient or to fill out a medical sheet, and registers the feature value as reference information. In the case where the feature value of the captured image of the face of the patient has been registered, the controller 11 determines that this patient is a follow-up patient, and adds the identification information of this patient to examination waiting-line data.

In addition, a modification according to the present invention may also be applied to management of health insurance cards at a medical institution. For example, the controller 11 stores, for each patient, a counter value indicating the number of monthly medical examinations of the patient in association with the reference information of the patient, and determines what number medical examination the current medical examination is for the patient from the counter value corresponding to the reference information corresponding to the feature value of the captured image of the face. The controller 11 causes the display 15 to display a message leading the patient to present his or her health insurance card in the case of the first medical examination of the month, and does not cause the display 15 to display the message in the case of the second or a subsequent medical examination of the month.

<Sixth Modification>

A modification according to the present invention may also be applied to withholding form printing. For example, the controller 11 counts, on an employee basis, the number of times a face verification has been performed since the date of issue of the latest withholding form, and may cause the display 15 to display a message leading an employee to print out his or her withholding form in the case where a captured image of the face of the employee is verified for the first time after the date of issue of the employee's latest withholding form.

In addition, the controller 11 counts, on an employee basis, the number of times a face verification has been performed in a certain period (a year, a half-year, a quarter of a year, or the like), and may cause the display 15 to display a briefing given from an owner at the beginning of the period in the case where a captured image of the face of an employee is verified for the first time in the period.

In addition, the controller 11 counts, on an employee basis, the number of times a face verification has been performed since the date when monthly travel expenses are reimbursed, and may cause the image forming unit 14 to print out a reimbursement document in the case where a captured image of the face of an employee is verified for the first time after the date when his or her monthly travel expenses are reimbursed.

<Seventh Modification>

A modification according to the present invention may also be applied to electronic devices other than printers.

The verification unit 101 may be provided outside an electronic device. In short, the modification according to the present invention may be specified as an information processing system including a verification unit that verifies biometric information acquired from users against preregistered reference information, and an execution unit that executes a process based on the number of times biometric information has been verified on a user basis in a predetermined period by the verification unit.

The examples in which the above-described functions are realized by the application program have been described in the exemplary embodiments; however, some of or all the above-described functions may be implemented as a hardware circuit. In addition, the application program may be provided via a computer readable recording medium, such as an optical recording medium or a semiconductor memory, on which the application program is recorded, and may be read out from this recording medium and installed. In addition, this program may also be provided through electric telecommunication lines.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing system for an electronic device, the system comprising:
 a memory storing biometric information of a plurality of users of the electronic device;
 a biometric capture device configured to capture an image including feature values corresponding to the biometric information of a current user; and
 a processor programmed to
  determine whether the feature values are included in the image captured by the biometric capture device,
  perform a verification process to determine whether the feature values in the captured image correspond to the biometric information of the plurality of users pre-stored in the memory, and
  increment a counter indicating a number of times within a predetermined period the verification process has been performed for the current user, wherein
 in response to the counter indicating that a current verification process is a first verification of the current user within the predetermined period, the processor records information regarding the current user in the memory and does not display a menu screen for operation of the electronic device by the current user, and
 in response to the counter indicating that the current verification process is a second or subsequent verification of the current user within the predetermined period, the processor displays the menu screen for operation of the electronic device by the current user.

2. The information processing system according to claim 1, wherein
 the processor performs authentication in accordance with a login operation, and displays the menu screen in a case where the second or a subsequent verification of the user has been performed and where authentication of the user performed has been successful.

3. An information processing method for an electronic device, the method comprising:
 storing, in a memory, biometric information of a plurality of users of the electronic device;
 capturing an image including feature values corresponding to the biometric information of a current user;
 determining whether the feature values are included in the captured image;
 performing a verification process to determine whether the feature values in the captured image correspond to the biometric information of the plurality of users pre-stored in the memory; and
 incrementing a counter indicating a number of times within a predetermined period the verification process has been performed for the current user, wherein
 in response to the counter indicating that a current verification process is a first verification of the current user within the predetermined period, information regarding the current user is recorded in the memory and a menu screen for operation of the electronic device by the current user is not displayed, and
 in response to the counter indicating that the current verification process is a second or subsequent verification of the current user within the predetermined period, the menu screen for operation of the electronic device by the current user is displayed.

4. An electronic device comprising:
 a memory storing biometric information of a plurality of users of the electronic device;
 a biometric capture device configured to capture an image including feature values corresponding to the biometric information of a current user; and
 a processor programmed to
  determine whether the feature values are included in the image captured by the biometric capture device,
  perform a verification process to determine whether the feature values in the captured image correspond to the biometric information of the plurality of users pre-stored in the memory, and
  increment a counter indicating a number of times within a predetermined period the verification process has been performed for the current user, wherein
 in response to the counter indicating that a current verification process is a first verification of the current user within the predetermined period, the processor records information regarding the current user in the memory and does not display a menu screen for operation of the electronic device by the current user, and
 in response to the counter indicating that the current verification process is a second or subsequent verification of the current user within the predetermined period, the processor displays the menu screen for operation of the electronic device by the current user.

* * * * *